US008076652B2

(12) United States Patent
Emmert et al.

(10) Patent No.: US 8,076,652 B2
(45) Date of Patent: Dec. 13, 2011

(54) REAL-TIME, ON-LINE ANALYSIS OF HALOACETIC ACID SPECIES AND AMOUNTS THEREOF IN DRINKING WATER SUPPLIES

(75) Inventors: Gary Lynn Emmert, Collierville, TN (US); Paul Steven Simone, Jr., Bartlett, TN (US)

(73) Assignee: The University of Memphis Research Foundation, Memphis, TN (US)

( * ) Notice: Subject to any disclaimer, the term of this patent is extended or adjusted under 35 U.S.C. 154(b) by 97 days.

(21) Appl. No.: 12/116,887

(22) Filed: May 7, 2008

(65) Prior Publication Data

US 2009/0278055 A1    Nov. 12, 2009

(51) Int. Cl.
*G01N 30/20* (2006.01)
(52) U.S. Cl. .................... 250/458.1; 73/61.56
(58) Field of Classification Search ............... 250/458.1; 73/61.56
See application file for complete search history.

(56) References Cited

U.S. PATENT DOCUMENTS

| | | | |
|---|---|---|---|
| 5,358,557 A | 10/1994 | Jiang et al. | |
| 5,492,838 A * | 2/1996 | Pawliszyn | 436/178 |
| 5,762,808 A | 6/1998 | Peyton | |
| 5,814,128 A | 9/1998 | Jiang et al. | |
| 5,911,882 A | 6/1999 | Benjamin et al. | |
| 6,106,725 A | 8/2000 | Hong | |
| 6,408,227 B1 | 6/2002 | Singhvi et al. | |
| 7,186,344 B2 | 3/2007 | Hughes | |
| 2004/0195181 A1* | 10/2004 | Loftis | 210/660 |
| 2005/0211643 A1* | 9/2005 | Phillips et al. | 210/753 |
| 2008/0226782 A1* | 9/2008 | Phillips et al. | 426/332 |
| 2010/0006513 A1* | 1/2010 | Fishler et al. | 210/755 |

OTHER PUBLICATIONS

Measuring the concentrations of drinking water disinfection by-products using capillary membrane sampling-flow injection analysis, Water Research 39 (2005) 3827-3836, G. Geme et al.
On-line monitoring of μg/L levels of haloacetic acids using ion chromatography with post-column nicotinamide reaction and fluorescence detection, Analytica Chemica Acta 570 (2006) 259-266, P.S. Simone, Jr. et al.

* cited by examiner

*Primary Examiner* — David Porta
*Assistant Examiner* — Djura Malevic
(74) *Attorney, Agent, or Firm* — Wyatt, Tarrant & Combs, LLP; William S. Parks

(57) ABSTRACT

Post-column reaction-ion chromatography (PCR-IC) analysis of drinking water samples for quantity measurements and species identification of haloacetic acid contaminants therein is provided. With the necessity to chlorinate drinking water to remove harmful bacteria and other potential toxins, haloacetic acid byproducts are generated that may harm humans after consumption as well. A reliable manner of measuring such drinking water supplies for haloacetic acids at locations far from the source and closer to dispensers is highly desirable. The PCR-IC analysis method of the invention has been found to be nearly as reliable as source measuring methods for the same purpose, but with the versatility to measure for such haloacetic acid contaminants anywhere along the drinking water supply line.

2 Claims, 3 Drawing Sheets

REAL-TIME, ON-LINE ANALYSIS OF HALOACETIC ACID SPECIES AND AMOUNTS THEREOF IN DRINKING WATER SUPPLIES

FIELD OF THE INVENTION

The present invention relates to post-column reaction-ion chromatography (PCR-IC) analysis of drinking water samples for quantity measurements and compound identification of haloacetic acid contaminants therein. With the necessity to chlorinate drinking water to remove harmful bacteria and other potential toxins, haloacetic acid byproducts are generated that may harm humans after consumption as well due to highly suspect carcinogenicity. A reliable manner of measuring such drinking water supplies for haloacetic acids at locations far from the source and closer to dispensers is highly desirable. The PCR-IC analysis method of the invention has been found to be nearly as reliable as source measuring methods for the same purpose, but with the versatility to measure for such haloacetic acid contaminants anywhere along the drinking water supply line.

BACKGROUND OF THE INVENTION

Drinking water has been, and continues to be, heavily treated for bacteria and other microscopic organisms that may cause infection in humans and other animals subsequent to consumption. In order to disinfect water supplies, halogenated materials have been introduced therein that have proven more than adequate for such a purpose. Unfortunately, although such halogenated compounds (chlorinated and chloraminated types, primarily) exhibit excellent disinfection capabilities, when present within aqueous environments at certain pH levels these halogenated compounds may generate byproducts that may themselves create health concerns. The United States Environmental Protection Agency (USEPA) in fact regulates five specific types of haloacetic acids within drinking water: monochloroacetic acid, dichloroacetic acid, trichloroacetic acid, monobromoacetic acid, and dibromoacetic acid. Removal of such compounds from drinking water is not possible as for typical chlorinated and brominated disinfecting compounds, at least not at the same reliability level as for the disinfecting agents. Thus, residual amounts may remain within treated water supplies that may require further removal processes to be undertaken. Of course, if the level of contamination is sufficiently low, initiation of such potentially expensive removal steps would be unwise from an economic perspective.

The USEPA currently has set a maximum contaminant level for these five haloacetic acids (collectively referred to as HAA5; four other haloacetic acids are currently not regulated by the USEPA, bromochloroacetic acid, bromodichloroacetic acid, dibromochloroacetic acid, and tribromoacetic acid; including these, the total haloacetic acid group is known as HAA9) at a total amount of 0.060 mg/L. It is thus important to reliably analyze and measure the total amount of such contaminants in order to determine if removal if necessary.

The USEPA has instituted its own testing methods for such a purpose. One, known as EPA 552.2, involves the liquid-liquid extraction of haloacetic acids from water sources into methyl-t-butyl ether, followed by derivatization with acidic methanol to form the corresponding haloacetic acid methyl esters. Analysis by gas chromatography-electron capture detection provides reliable measurements of the haloacetic acid amounts present within the subject water supply. The other, USEPA 552.3, is a derivative of the first with optimizations of acidic methanol neutralization procedures for improvement in brominated trishalogenated haloacetic acid species. These general processes have been found to have numerous drawbacks, however. For instance, injection port temperature can affect debromination of certain haloacetic acid species (particularly tribrominated types) that may lead to under-representation of the amount of such contaminants present within the tested water source. Likewise the water content of the methyl-t-butyl ether extract may decarboxylate the haloacetic acids, again leading to an under-reporting of the actual amounts present within the test sample. Furthermore, the involved processing needed to actually undergo such analysis makes an on-line protocol rather difficult to implement, particularly when hourly sampling is necessary. Other derivatization methods have been either followed or suggested for gas chromatography analyses of drinking water sources as well, including utilizing diazomethane, acidic ethanol, and aniline. Such reactant-based measurements, however, all suffer the same time and labor-intensive problems as with the two EPA test procedures noted above. As such, on-line analysis through these protocols are difficult, expensive, and labor intensive to implement.

Measurement at the source (i.e., within a water purification plant location) may be effective for system-wide average readings; however, in the large supplies of water at such locations, the chances of proper sampling to that effect may be suspect since the contaminants may be present in varied locations, rather than definitely mixed throughout the tested water supply itself. Additionally, testing may not uncover the actual level of residual haloacetic acid disinfection byproducts prior to the water supply being disbursed to distant dispense sites (transfer pipes, homes, schools, businesses, etc.). In any event, there is a relatively new rule in place that requires utilities to provide evidence of compliance with haloacetic acid levels at multiple locations, rather than a straightforward system-wide average. Thus, since the above-described derivatization procedures with gas chromatography-electron capture detection analytical methods are not suitable for a uniform haloacetic acid measurement scheme. There is thus a drive to implement remote testing via real-time, on-line methods for water supply HAA5, and, more importantly, for HAA9 contaminant level measurements.

Such a desirable on-line procedure has been difficult to achieve, however, particularly as it pertains to the determination of not only the amount of HAA9 within water supplies, but also the amount of each species of the HAA9 group present within the tested water source. High performance liquid chromatography, utilizing electrospray ionization-mass spectrometry or ultraviolet absorbance as the detector, has been attempted, as well as ion chromatography, with membrane-suppressed conductivity detection or, as well, ultraviolet absorbance detection. Other attempts with inductively coupled plasma-mass spectrometry and electrospray ionization-mass spectrometry coupled with ion chromatography have been followed as well for this same purpose. The detection level can be as low as 0.5 to less than 10 µg/L for HAA9 species, but only subsequent to sample preparations. The sensitivity and selectivity of ion chromatography and high performance liquid chromatography methods are easily sacrificed without the cumbersome preparations in place, therefore requiring operator intervention during analysis. Again, this issue leads to serious drawbacks when on-line implementation is attempted as well.

Another methodology that has proven effective to a degree is post-column reaction-ion chromatography. This has shown promise, but only in terms of quantifying bromate ion concentrations in drinking water samples at a single microgram per liter level. This dual selectivity form (separation by ion chromatography column as well as the selective reaction with the post-column reagent with the analyte) offers an advantageous test method over the others noted above, except for the presence of more common anions, specifically chloride, at much higher concentrations within the sampled drinking water supply (mg/L instead of µg/L). It was then undertaken to combine the separation capabilities of ion chromatography with the reaction of the haloacetic acid species with nicotinamide, followed by fluorescene detection to measure the individual and total HAA5 concentrations in drinking water at the single µg/L level. The problem with such a protocol, unfortunately, was that bromochloroacetic acid interfered with dichloro- and dibromo-acetic acid quantifications. Despite this problematic limitation, it was determined that fluorescence detection provided a much improved detection protocol in comparison with ultraviolet absorbance and mass spectrometry possibilities. Thus, although such a fluorescence method of detection, coupled with the post-column reaction (again with nicotinamide reagent) and ion chromatography, exhibited the best results in terms of an on-line test method for HAA5 drinking water contaminant measurement levels, there remained a definite need for improvements in total haloacetic acid measurements and identifications within such test samples. To date, however, there has not been an analytical test protocol that has permitted implementation of such a system within an on-line real-time monitoring procedure with an acceptable degree of reliability.

ADVANTAGES AND SUMMARY OF THE INVENTION

Accordingly, it is an advantage of the present invention to provide a reliable on-line drinking water analytical protocol for determining both the identity and individual measurements for the nine different haloacetic acids that are commonly present as disinfection byproducts within such water sources. It is an additional advantage of the invention to provide reliability similar to that exhibited by USEPA test methods 552.2 and 552.3, but at any location along a drinking water supply line and without need for operator involvement.

Accordingly, the instant invention encompasses a method of analyzing drinking water samples comprising the steps of:

a) providing at least one stream of drinking water that has been disinfected with chlorinated or chloraminated materials;

b) delivering said at least one stream of drinking water through at least one anion exchange column with a suitable buffer to separate individual haloacetic acids from said at least one stream of drinking water from one another;

c) delivering said separated haloacetic acids to a mixing manifold and introducing therein a fluorescing compound for reaction with each of said separated individual haloacetic acids; and d) delivering the separated fluorescing haloacetic acids to a fluorescence detection to determine the amount of each separate haloacetic acid within the at least one initial drinking water stream through fluorescence detection.

Also encompassed within this invention is a drinking water analytical instrument comprising an eluent injection line, a drinking water sample injection line, a six-port valve, wherein said valve permits mixing of eluent and drinking water sample therein at certain levels of drinking water sample amounts, at least one anion exchange column connected to said valve, a mixing manifold attached to said column via a feed line, and a fluorescence detector attached to said mixing manifold via a second feed line.

For this overall method to properly function in a real-time on-line capacity, the chromatograph must be configured in such a manner that minimal operator involvement is required and repetition of the measurements sought can be performed uniformly over an extended time period. Such has been permitted through the utilization of the critical fluorescence detection procedure subsequent to separation of the individual haloacetic acids from the drinking water samples. The initial IC allows for such separation prior to reaction with the nicotinamide. These separated compounds can then be identified via fluorescence detection as well. As noted above, however, the criteria for determination of effectiveness of such an analytical method included not only identification of the different HAA9 compounds, but also the concentrations of these individual compounds that may potentially be present as disinfection byproducts within the drinking water samples. Of great importance then was the ability of such measurement methods to record the concentrations thereof at reliable levels (within a certain bias as compared with other standard measuring processes, such as EPA 552.3) and for both chlorinated and chloraminated water samples (since these types of disinfectants are the most widely utilized types in water systems).

Such methods have permitted implementation of remote automatic testing procedures and instrumentation along any location of a drinking water supply line. As noted above, the previous analytical approaches suffered necessary operator involvement, deleterious effects from reactants or simultaneously formed byproducts thwarting reliable measurements from being taken, as well as lack of actual identification of each byproduct to ensure compliance with governmental regulations. This present method has overcome such limitations through the refinement of the fluorescing step coupled with a remote detection process and reliable separation procedure. The instrumentation does not require human operator involvement unless a breakdown or energy source failure occurs; for testing purpose, however, the analyses can be performed at regular intervals through computer processor control.

In order to attain such levels of reliability, the measurements of the HAA9 amounts had to be comparable to those provided through the aforementioned USEPA 552 series test protocols. As well, the ability to permit identification of the HAA9 compounds within the target drinking water sample must be at such a level that proper discernment of each individual compound is necessary as well. Such has been attained with this inventive method.

DETAILED DESCRIPTION OF THE DRAWINGS AND PREFERRED EMBODIMENTS OF THE INVENTION

Figure 1:
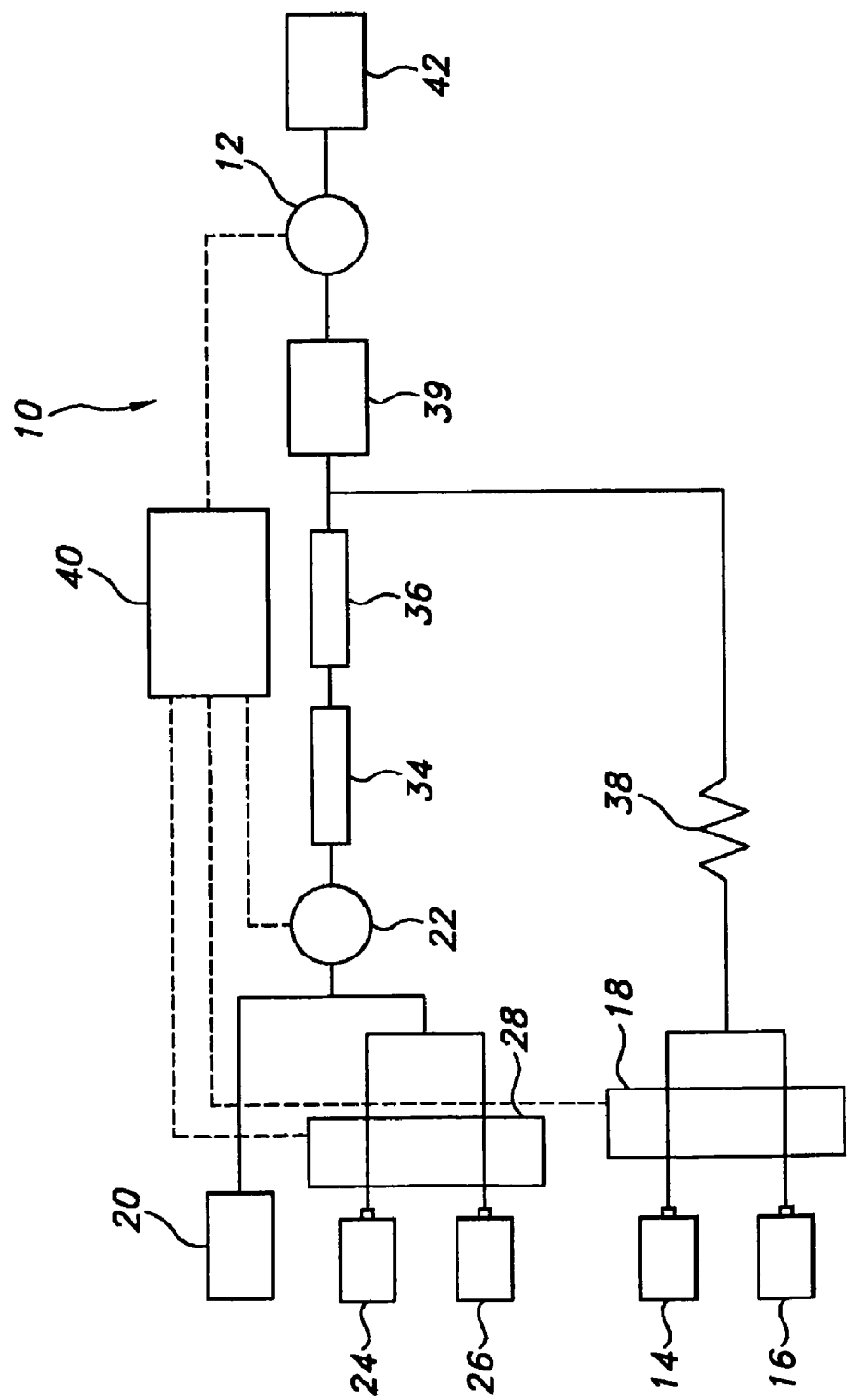
FIG. 1 depicts a schematic of the post-column reaction-ion chromatography analyzer with a six-port valve utilized for the on-line inventive HAA9 measurement and identification procedure.
Figure 2:
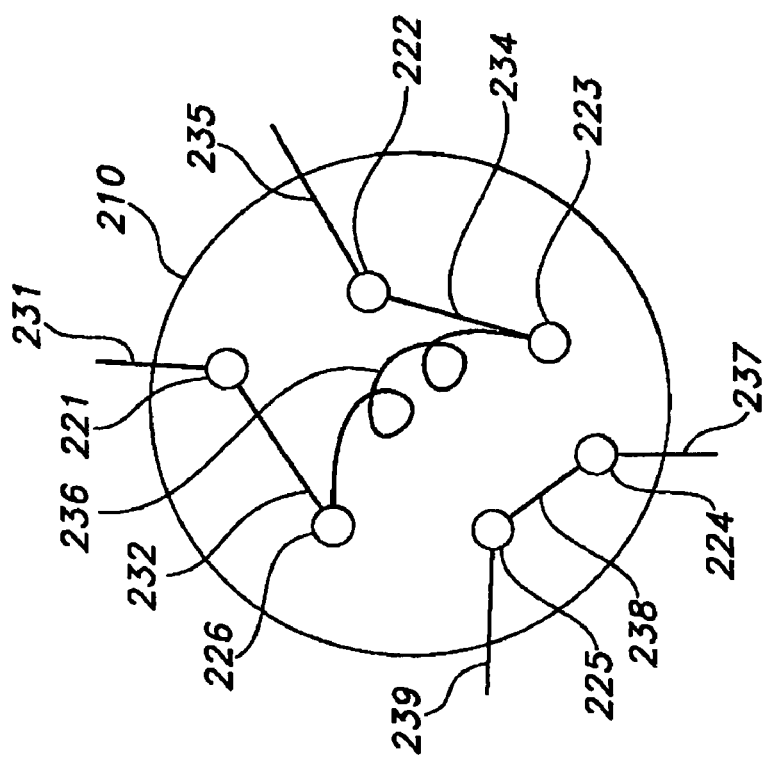
FIG. 2 depicts the six-port valve of FIG. 1 in closer view.
Figure 3:
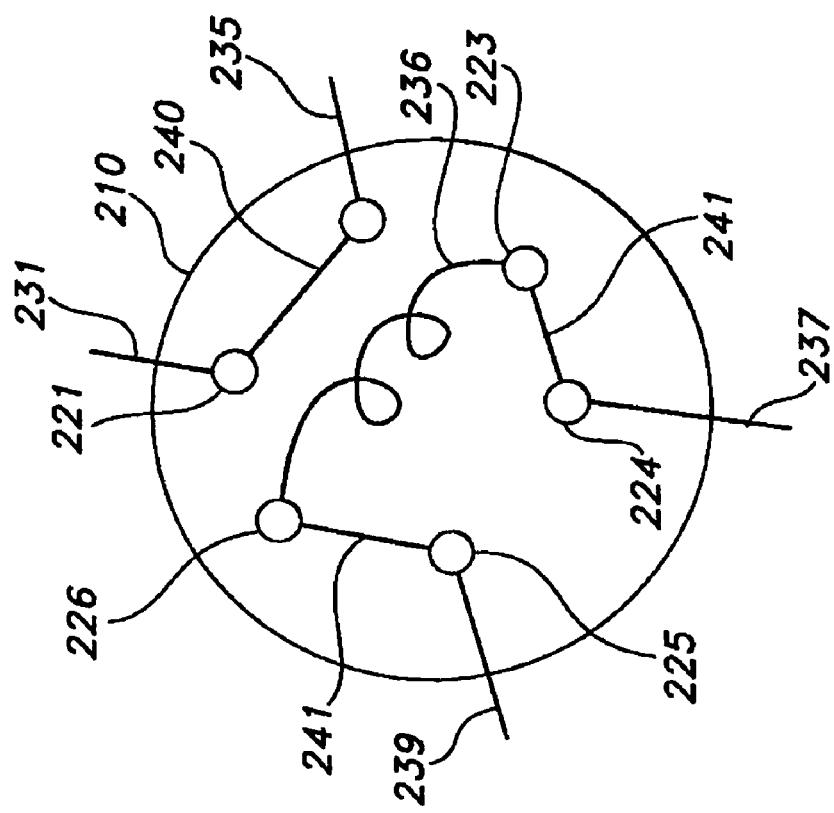
FIG. 3 depicts a different alternate position of the same six-port valve of FIG. 2.

As shown in FIG. 1, the overall system basically includes a PCR-IC analyzer 10 including a fluorescence detector 12 (available from Waters, Dionex, Shimadzu, etc.) through which the fluoresced HAA9 compounds pass to determine amounts and identifications thereof. Initially, within this instrumentation, a sodium hydroxide (NaOH) (2.0 M, preferably, though not necessarily) stream 14 and a stream of preferably, though not necessarily, 37.5% aqueous solution of nicotinamide 16 are introduced within the device through a pump 18 (such as, preferably, though not necessarily, a peristaltic pump, from FIA Lab) that controls the flow rate thereof each reagent. The water samples were introduced through a separate stream 20 and are transported to a six-port valve 22 (from VICI, Inc.) including, preferably, a 2000 microliter sample loop (236 in FIGS. 2 and 3). This valve 22 controls the injection of eluent and amount and timing of sample injection to be tested within the PCR-IC analyzer. In load position (as shown in FIG. 2, below), the water samples are allowed to circulate within the valve 210 (FIGS. 2 and 3) from the sample injection line 231 into the first port 221 then to the sixth port 226 through a second line 232, through the sample loop 236 to the third port 223, through a fourth line 234 to the second port 222, to the sample waste line 235, ultimately to a waste receptacle (not illustrated). In this load position, the eluent is delivered to the valve 210 through the eluent injection line 237 into the fourth port 224, through an eighth line 238 to the fifth port 225, and out to the PCR-IC through the exit line 239. At this point, the eluent is the only stream passing through the PCR-IC. The eluent itself is comprised of a buffer stream (24 of FIG. 1) (any suitable buffer is possible as long as such buffer effectuates proper exchange within the column or columns of the instrument), as well as a reagent (purified) water stream (26 of FIG. 1). The valve 210 (FIGS. 2 and 3) may be reconfigured through a rotating disk (not illustrated) attached to an actuator (not illustrated) that is controlled by the overall computer system (40 in FIG. 1). Upon reconfiguration, the valve 210 will move to an inject position whereby the water sample stream will pass directly from the first port 221 to the second port 222 via a tenth line 240, thereby sending the water stream directly to the waste receptacle (not illustrated). Two other different lines 241, 242 then permit delivery of the eluent stream through the loop 236 as well. At the instant the valve 210 is reconfigured to inject position, the remaining haloacetic acid water sample stream within the loop 236 will be mixed with the eluent stream that is now passing through the same loop 236 through the sixth and fifth ports 226, 225 consecutively and out the exit line 239 for delivery to the PCR-IC analysis devices (28, 30, 32 in FIG. 1). This injection lasts for anywhere from 0.5 to 10 minutes, although a four-minute duration is preferred. (The entire timeframe of testing may be from 15 minutes to 24 hours, in terms of the passage of the sample stream through the columns and the fluorescent detector, with a duration of 1-3 hours, and preferably, about 2 hours, or 120 minutes; thus, the injection of the water stream into the analytical device is only 4 minutes of a total potential 120 minute cycle).

Returning to FIG. 1, the reagent water stream 26 is mixed with the buffer stream 24 (preferably, though not necessarily, 400 mM $H_3BO_3$ buffer mixed with 80 mM NaOH) via a gradient pump 28 (such as a Dionex GPM-1) set at any flow rate, though preferably at about 0.5 mL/min. The gradient pump 28 is set to provide a preferred programming of borate buffer modifications whereby the initial concentration of buffer was 1% throughout a 4-minute sample injection time. The next four minutes, the borate buffer increased to 13% concentration and held until the 22 minute mark had been reached. For one minute thereafter, the % buffer increased to 20% and remained there until the 28 minute mark. From the 28 to 35 minute mark, the buffer increased in concentration to 40%, then for the next ten minutes, to 70%, for the next five minutes to 90%, and finally for the next three minutes up to 100%, at which time that level was retained until the 90 minute mark. Subsequently, the buffer level returned to 1% over the next ten minute period, and was held at that level until 120 minutes had passed. At that point, the injection program began over again.

After the valve 22, the line of either water sample or buffered reagent water moves to a series of ion chromatography columns, preferably, the first being a guard column 34 (Dionex AG9) (50 mm by 4 mm in dimensions), and followed by two analytical columns 36 (Dionex AS9-SC) (250 mm by 4 mm in dimensions) (pictured as one component). Simultaneously the pump 18 (again, preferably, though not necessarily, a four-channel peristaltic pump, such as from FIALab 2500) transports the two separate streams of 2.0 M NaOH 14 and 37.5% aqueous nicotinamide 16, that are then mixed within a mixing coil 38 (preferably a knitted open-tubular mixing device) and transported to a mixing device 39 (such as a knitted open-tubular mixing device) (0.75 inner diameter) (and preferably four such mixing coils in series being 10 meters in length) (from SeQuant AB) which is placed within a heated water bath (not illustrated) at about 97° C. (although any temperature may be employed; the higher the temperature, the faster the overall reaction, generally). The resultant heated fluorescing HAA9 compounds (after reaction with the nicotinamide with the sodium hydroxide aiding in intensity increase) are then moved through the fluorescent detector 12, with a waste receptacle 42 available for dispensing of the tested stream. The fluorescence detector 12 exhibited an excitation wavelength over the range of 355 to 380 nm, preferably 365 nm and an emission wavelength over the range 430 to 500 nm, preferably 455 nm. Typically, the individual HAA9 compounds eluted within the column at different times in order to properly identify each compound as well as the amounts present within the sample water. Thus, monochloroacetic acid eluted at about 58 minutes under this protocol, monobromoacetic acid at about 59 minutes, dichloroacetic acid at about 66 minutes, bromochloroacetic acid at about 68 minutes, dibromoacetic acid at about 70 minutes, trichloroacetic acid at about 85 minutes, bromodichloroacetic acid at about 88 minutes, dibromochloroacetic acid at about 94 minutes, and trichloroacetic acid at about 101 minutes. As the total run time was about 120 minutes, this was sufficient for a full test to be completed. This elution point for each compound was measured as the retention time for a compound from the time the sample was injected within the valve 12 until it was detected by the fluorescent detector 12 (and included both separation and post-column reaction time). The entire system is controlled via computer 44 for full automation and no need for direct operator involvement.

In this manner, the HAA9 compounds can be easily separated via IC, then reacted, fluoresced, and measured through PCR. Such a system can be implemented at any location and, through automation, does not require continued operator input or control. The peristaltic pumps are also controlled through computer software or other type of automation, thereby allowing, again, for remote utilization. The main issue in terms of proper selectivity of such a system for such a purpose is the reliability thereof at such remote locations. In order to determine the feasibility of such an analytical method, it was first necessary to compare the results thereof to standard USEPA methods.

For HAA5 measurements, one specific federal regulatory test method has been followed by water utilities for compliance, albeit from the water source itself. In terms of such source measurements, however, this standard (USEPA 552.3 test protocol) has been the most reliable. Comparisons of drinking water samples for similar measurements through this compliance standard test and those of the instant inventive method were undertaken. If the measurements were actually similar in amounts, identifications, and standard deviations, it would be properly assumed that the new method would be significantly reliable to the degree required under Federal regulations.

The USEPA Method 552.3 measures HAA9 concentrations in drinking water only. As noted above, liquid-liquid extraction was undertaken into methyl-t-butyl ether, followed by derivatization of the resultant compounds with acidic methanol into methyl esters of the HAA9 compounds. These compounds were then analyzed via GC-ECD wherein the GC was a Varian 3380 equipped with a Ni-63 ECD detector. The MDL values for the HAA9 compounds were, respectively for monochloroacetic acid (MCAA), dichloroacetic acid (DCAA), trichloroacetic acid (TCAA), monobromoacetic acid (MBAA), dibromoacetic acid (DBAA), bromochloroacetic acid (BCAA), bromodichloroacetic acid (BDCAA), dibromochloroacetic acid (DBCAA), and tribromoacetic acid (TBAA), were (in µg/L) 0.3, 0.2, 0.2, 0.1, 0.4, 0.2, 0.3, 0.4, and 0.5. The mean recoveries were, respectively, (in percentages) 119, 117, 64.5, 161, 89.5, 76.9, 101, 93.1, and 94.1. Also, the relative standard deviation values were, again, respectively, (in percentages) 2.1, 1.0, 2.3, 0.6, 3.5, 3.5, 2.9, 3.5, and 4.6.

Thus, as noted above, it was important that the system devised exhibit similar results for these measurements. However, optimization of the separation capabilities and collection of only the compounds for which measurement and identification were necessary was required initially. Fluorescent intensity needed to be improved to the level that detection would permit effective measurements. The sodium hydroxide carrier stream was of great criticality in increasing this intensity. The preferred 2M NaOH was thus determined to meet this requirement.

Thus, after such optimization was put in place, drinking samples were then tested in accordance with the device described supra. Initial standards of different concentrations were then prepared of the HAA9 compounds in order to generate calibration curves thereof. As is customary, the peak height of the chromatogram of each individual HAA9 compound is plotted as a function of concentration. In terms of these initial calibration studies, the MDLs of each compound were very promising in comparison with those of the USEPA Test Method 522.3, undertaken and described above. The MDL values for the HAA9 compounds were, respectively for monochloroacetic acid (MCAA), dichloroacetic acid (DCAA), trichloroacetic acid (TCAA), monobromoacetic acid (MBAA), dibromoacetic acid (DBAA), bromochloroacetic acid (BCAA), bromodichloroacetic acid (BDCAA), dibromochloroacetic acid (DBCAA), and tribromoacetic acid (TBAA), were (in microgram/liter) 2.2, 6.6, 2.1, 2.1, 3.2, 0.6, 2.8, 5.6, and 10.1. The mean recoveries were, respectively, (in percentages) 83, 90, 79, 94, 58, 86, 82, 91, and 161. Also, the relative standard deviation values were, again, respectively, (in percentages) 13, 25, 12, 11, 26, 3.5, 17, 32, and 29. The calibration curves thus provided an acceptable measuring stick with which to plot the concentrations of the actual unknown drinking water sample values for the HAA9 compounds.

Within both chlorinated and chloraminated treated water systems, samples were drawn and tested within the inventive system and the 552.3 test method. For the chlorinated water samples, the testing was performed . . . .

Within both chlorinated and chloraminated treated water systems, samples were drawn and tested within the inventive system and the 552.3 test method. For the chlorinated water samples, the testing was performed over a 131 hour period; for the chloraminated, a 71 hour time period. Concentrations HAA9 were monitored at a rate of 1 sample per two hours (with every $12^{th}$ hour excluded in order to run a standard control) through the inventive analyzer; and 1 sample per hour for the USEPA method. For the first two days of sampling, measurements were taken every hour, followed by one sample every two hours thereafter. (Assuming that the 552.3 test method provided the "true value" of the level of contaminants (here individual HAA9 and total HAA9), a bias was calculated as a comparison therewith the 552.3 results, being the inventive results minus each individual 552.3 test method result.

For 47 direct comparisons for all HAA9 species, the concentration of monochloroacetic acid ranged from 0.3-1.3 µg/L with an average of 0.3±0.1 µg/L using EPA 552.3. The PCR-IC reported a concentration range from 1.7 to 13.7, and the average concentration of 2.7±2.0 µg/L. The PCR-IC bias ranged from 0.4 to 13.4 µg/L. The average bias was 2.4±2.0 µg/L.

The concentration of dichloroacetic acid ranged 1.6-2.8 µg/L using EPA 552.3, and 6.6-11.1 µg/L using PCR-IC. The average concentration was 1.9±0.2 µg/L using the EPA 552.3, and 6.8±0.9 µg/L using PCR-IC. The PCR-IC bias ranged from 3.8-9.2 g/L with an average of 4.9±0.9 µg/L.

Trichloroacetic acid concentrations ranged from 0.2-0.5 µg/L using EPA 552.3, and 2.1-4.1 µg/L using PCR-IC. The average concentration was 0.2±0.0 µg/L using EPA 552.3, and 2.2±0.3 µg/L using PCR-IC. The PCR-IC bias ranged from 1.6 to 3.9 µg/L with an average of 2.0±0.3 µg/L.

The concentration of monobromoacetic acid ranged from 0.1-1.0 µg/L using EPA 552.3, and 2.1-4.8 µg/L using PCR-IC. The average concentration was 0.5±0.3 µg/L using EPA 552.3, and 2.2±0.5 µg/L using PCR-IC. The PCR-IC bias ranged from 1.1 to 4.7 µg/L with an average of 1.7±0.6 µg/L).

Dibromoacetic acid concentrations ranged from 0.4-1.0 µg/L using EPA 552.3, and 2.6-4.8 µg/L using PCR-IC. The average concentration reported by EPA 552.3 was 0.4±0.1 µg/L, and for PCR-IC was 2.7±0.4 µg/L. The PCR-IC bias averaged 2.3±0.4 µg/L and ranged from 1.6-4.4 µg/L.

The concentration of bromochloroacetic acid ranged from 0.4-0.9 µg/L for USEPA 552.3, and 0.6-14.1 µg/L for PCR-IC. The average concentration for EPA 552.3 and PCR-IC was 0.5±0.1 µg/L 1.4±2.2 µg/L, respectively. The PCR-IC bias ranged from −0.3-13.7 µg/L with an average of 0.9±2.2 µg/L.

Bromodichloroacetic acid was not detected and thus the concentrations were expected to be below the MDL for BDCAA. This was true for both EPA 552.3 and PCR-IC.

Dibromochloroacetic acid concentrations were less than the MDL for USEPA 552.3. However, for PCR-IC, the concentration ranged from 5.6-8.5 µg/L. The average concentration using PCR-IC was 5.7±0.5 µg/L. The PCR-IC bias, using the MDL value for EPA 552.3 as the "true value", ranged from 5.3-8.2 µg/L with an average of 5.3±0.5 µg/L.

Tribromoacetic acid concentrations ranged from 0.5-0.6 µg/L using EPA 552.3, and 10.1-12.2 µg/L using PCR-IC. The average concentration was 0.5±0.0 µg/L using EPA 552.3, and 10.2±0.4 µg/L using PCR-IC. The PCR-IC bias ranged from 9.5-11.7 µg/L (with an average of 9.7±0.4 µg/L).

Total HAA9 ranged from 2.1-7.6 µg/L using EPA 552.3, and 0.0-39.7 µg/L using PCR-IC. The average total HAA9 concentration was 3.0±0.8 µg/L using EPA 552.3, and 9.5±9.7 µg/L using PCR-IC. The PCR-IC bias for total HAA9 ranged from −2.9-36.9 µg/L with and average of 6.5±9.7 µg/L.

The chloraminated water study had 21 comparisons for dichloroacetic acid, dibromoacetic acid, bromochloroacetic acid and total HAA9. There were 23 comparisons for the remainder of the HAA9 species.

For the monochloroacetic acid, the concentration ranged from 2.1 to 6.1 μg/L with an average of 3.8±1.4 μg/L using EPA 552.3. The PCR-IC method measured concentrations ranging from 2.7 to 15.3 with an average concentration of 8.6±3.8 μg/L. The PCR-IC bias ranged from −2.9 to 13.2 μg/L for the PCR-IC with an average bias of 4.8±4.8 μg/L.

Dichloroacetic acid concentrations ranged from 34.1-45.7 μg/L using EPA 552.3, and 9.8-46.8 μg/L for PCR-IC. The average concentration was 42.1±2.7 μg/L for EPA 552.3, and 27.5±9.8 μg/L for PCR-IC. The PCR-IC bias ranged from −34.5-3.0 μg/L with an average of −14.7±10.0 μg/L.

The concentration of trichloroacetic acid ranged from 16.5-28.4 μg/L using EPA 552.3, and 2.0-14.2 μg/L for PCR-IC for 23 direct comparisons. The average concentration was 18.7±2.4 μg/L using EPA 552.3, and 7.7±4.2 μg/L using PCR-IC. The PCR-IC bias ranged from −25.1 to −4.5 μg/L with an average of −11.0±5.2 μg/L.

The monobromoacetic acid concentration ranged from 0.1-2.3 μg/L using EPA 552.3, and 2.1-7.8 μg/L using PCR-IC. The average concentration was 1.6±0.7 μg/L using EPA 552.3, and 2.3±1.2 μg/L, using PCR-IC. The PCR-IC bias ranged from −0.2 to 5.7 μg/L with an average of 0.7±1.3 μg/L).

The dibromoacetic acid concentrations were less than the MDL of 0.4 μg/L for all EPA 552.3 samples. For PCR-IC, the concentration ranged from 3.2-6.0 μg/L. with an average concentration for PCR-IC of 3.5±0.8 μg/L. The PCR-IC bias using the EPA 552.3 MDL values (0.4 μg/L) as the "true values" ranged from 2.8-5.7 μg/L with an average of 3.1±0.8 μg/L.

The concentrations of bromochloroacetic acid ranged from 5.8-7.4 μg/L using EPA 552.3, and 0.6-3.1 μg/L using PCR-IC. The average concentration was 6.5±0.5 μg/L using EPA 552.3, and 1.9±0.6 μg/L using PCR-IC. The PCR-IC bias ranged from −6.7 to −3.1 μg/L with an average of −4.6±0.9 μg/L.

Bromodichloroacetic acid concentrations ranged from 3.2-4.9 μg/L using EPA 552.3, and 2.8-3.8 μg/L using PCR-IC. The average BDCAA concentration was 4.2±0.4 μg/L using EPA 552.3, and 2.8±0.2 μg/L using PCR-IC. The PCR-IC bias ranged from −2.1 to −0.1 μg/L with an average of −1.4±0.5 μg/L.

Dibromochloroacetic acid was not detected using either EPA 552.3 or PCR-IC methods. The concentration was less than the MDL of 0.4 μg/L for EPA 552.3 and the MDL of PCR-IC (5.6 μg/L).

Tribromoacetic acid concentrations ranged from 0.5-0.7 μg/L using EPA 552.3, and were less than the MDL of 10.1 using the PCR-IC method. The average concentration using EPA 552.3 was 0.6±0.1 μg/L. The bias, using the MDL for PCR-IC as the experimental value, ranged from 9.4-9.6 μg/L with an average of 9.5±0.1 μg/L.

The total HAA9 concentration ranged from 69.1-83.0 μg/L using EPA 552.3, and 33.6-67.8 μg/L using PCR-IC. The average total HAA9 concentration was 77.4±3.3 μg/L using EPA 552.3, and 49.7±8.5 μg/L using PCR-IC. The PCR-IC bias for total HAA9 ranged from −42.3 to −8.7 μg/L with an average of −27.7±8.1 μg/L.

Furthermore, the larger negative bias results for the 552.3 test method comparisons are expected as this USEPA test protocol requires storage of water samples after addition of ammonium chloride crystals thereto. After time, these crystals would undoubtedly react with other types of halogenated compounds within the water sample to generate larger concentrations of HAA9 compounds therein. As such, the resultant negative bias levels most likely show that the on-line system (real-time in effect) of the PCR-IC inventive analytical method provides a more reliable, or, at least, comparable measuring procedure in comparison with the Federal regulatory compliance standards.

The preceding examples are set forth to illustrate the principles of the invention, and specific embodiments of operation of the invention. The examples are not intended to limit the scope of the method. Additional embodiments and advantages within the scope of the claimed invention will be apparent to one of ordinary skill in the art.

What we claim is:

1. A method of analyzing drinking water samples comprising the steps of:
   a) providing at least one stream of drinking water that has been disinfected with chlorinated or chloraminated materials;
   b) delivering said at least one stream of drinking water through at least two anion exchange columns present in a series with a suitable buffer to separate all individual haloacetic acids, listed as monochloroacetic acid (MCAA), dichloroacetic acid (DCAA), trichloroacetic acid (TCAA), monobromoacetic acid (MBAA), dibromoacetic acid (DBAA), bromochloroacetic acid (BCAA), bromodichloroacetic acid (BDCAA), dibromochloroacetic acid (DBCAA), and tribromoacetic acid (TBAA), present within said at least one stream of drinking water from one another;
   c) delivering said separated haloacetic acids to a mixing manifold and introducing therein a fluorescing compound for reaction with each of said separated individual haloacetic acids to provide separate fluorescing haloacetic acids;
   d) heating said separate fluorescing haloacetic acids; and
   e) delivering the separated fluorescing haloacetic acids to a fluorescence detector to determine the amount of each separate haloacetic acid within the at least one initial drinking water stream through fluorescence detection;
   wherein said method permits separate elution of monochloroacetic acid and monobromoacetic acid to permit proper and separate measurement of each haloacetic acid present within said drinking water to a measurement level of μg/L.

2. A drinking water analytical instrument comprising an eluent injection line, a drinking water sample injection line, a six-port valve, wherein said valve permits mixing of eluent and drinking water sample therein at certain levels of drinking water sample amounts, at least two anion exchange columns in a series with only one connected to said valve, a mixing manifold attached to said valve via a feed line, and a fluorescence detector attached to said mixing manifold via a second feed line.

* * * * *